US009192922B2

(12) United States Patent
Midorikawa et al.

(10) Patent No.: US 9,192,922 B2
(45) Date of Patent: Nov. 24, 2015

(54) PROPYLENE PRODUCTION PROCESS (75) Inventors: Hideo Midorikawa, Tokyo (JP); Takashi Tsunoda, Tokyo (JP); Kenji Akagishi, Tokyo (JP); Hiroyuki Yano, Tokyo (JP); Ryusuke Miyazaki, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 457 days.

(21) Appl. No.: 12/678,740

(22) PCT Filed: Sep. 9, 2008

(86) PCT No.: PCT/JP2008/066236
§ 371 (c)(1),
(2), (4) Date: Mar. 17, 2010

(87) PCT Pub. No.: WO2009/037992
PCT Pub. Date: Mar. 26, 2009

(65) Prior Publication Data
US 2010/0197986 A1    Aug. 5, 2010

(30) Foreign Application Priority Data

Sep. 18, 2007  (JP) ................................ 2007-241434
Mar. 13, 2008  (JP) ................................ 2008-064843

(51) Int. Cl.
*C07C 1/20* (2006.01)
*B01J 29/42* (2006.01)
*B01J 29/06* (2006.01)
*B01J 29/40* (2006.01)
*B01J 29/90* (2006.01)
*B01J 35/00* (2006.01)
*B01J 35/02* (2006.01)
*B01J 35/10* (2006.01)
*B01J 37/00* (2006.01)
*B01J 37/28* (2006.01)
*C07C 4/06* (2006.01)

(52) U.S. Cl.
CPC  *B01J 29/42* (2013.01); *B01J 29/06* (2013.01); *B01J 29/40* (2013.01); *B01J 29/90* (2013.01); *B01J 35/002* (2013.01); *B01J 35/0026* (2013.01); *B01J 35/023* (2013.01); *B01J 35/10* (2013.01); *B01J 37/0009* (2013.01); *B01J 37/0036* (2013.01); *B01J 37/0045* (2013.01); *B01J 37/28* (2013.01); *C07C 1/20* (2013.01); *C07C 4/06* (2013.01); *B01J 2229/42* (2013.01)

(58) Field of Classification Search
CPC .................................... C07C 2/00; C07C 1/20
USPC ......... 585/640, 648, 650, 651, 653, 638, 639, 585/641, 642; 502/64, 68, 70, 71, 77; 423/700; 208/109, 113, 114, 118
See application file for complete search history.

(56) References Cited

U.S. PATENT DOCUMENTS

| 3,926,782 | A | 12/1975 | Plank et al. |
| 4,650,654 | A | 3/1987 | Arika et al. |
| 5,110,776 | A | 5/1992 | Chitnis et al. |
| 5,194,412 | A | 3/1993 | Roberie et al. |
| 6,385,437 | B1 | 5/2002 | Park et al. |
| 6,388,161 | B1 | 5/2002 | Dath et al. |
| 7,262,332 | B2 | 8/2007 | Duplan et al. |
| 7,608,746 | B2 | 10/2009 | Setoyama et al. |
| 2004/0266608 | A1 * | 12/2004 | Long et al. ........................ 502/68 |
| 2005/0222475 | A1 * | 10/2005 | Duplan et al. ................. 585/329 |
| 2005/0227853 | A1 | 10/2005 | Kumar |
| 2007/0260096 | A1 * | 11/2007 | Vaughn et al. ................... 585/17 |
| 2008/0093263 | A1 | 4/2008 | Cheng et al. |
| 2010/0222203 | A1 | 9/2010 | Baba et al. |
| 2010/0256316 | A1 * | 10/2010 | Vermeiren et al. ............... 502/64 |

FOREIGN PATENT DOCUMENTS

| CA | 1018189 | 9/1977 |
| EP | 0 496 226 A1 | 7/1992 |

(Continued)

OTHER PUBLICATIONS

Supplementary European Search Report dated Dec. 15, 2010 issued in corresponding International Application No. PCT/JP2008066236.
International Search Report from Japanese Patent Office for International Application No. PCT/JP2008/066236, Mailed Dec. 16, 2008.
Lide, D. R. et al., "CRC Handbook of Chemistry and Physics, A Ready-Reference Book of Chemical and Physical Data," Handbook of Chemistry and Physics, CRC Press, Inc., 75th Edition, p. 1-15, (1994-1995).
International Preliminary Report on Patentability dated Apr. 15, 2010.

*Primary Examiner* — In Suk Bullock
*Assistant Examiner* — Sharon Pregler
(74) *Attorney, Agent, or Firm* — Finnegan, Henderson, Farabow, Garrett & Dunner, L.L.P.

(57) ABSTRACT

The present invention provides a process for producing propylene, comprising contacting at least one of raw material selected from the group consisting of ethylene and ethanol with a catalyst containing a medium pore diameter zeolite in a fluidized bed reactor wherein the catalyst containing the medium pore diameter zeolite satisfies the following (a) through (e):

(a) a particle diameter of catalyst particles at 90% by weight or more is within a range of 10 to 197 μm;
(b) a bulk density of the catalyst particles is within a range of 0.7 to 1.1 g/cm$^3$;
(c) a mean compressive strength of the catalyst particles having a particle diameter within a range of 30 to 70 μm is 15 MPa or more, and a compressive strength of the catalyst particles at 90% by weight or more is 10 MPa or more;
(d) an angle of repose is 20 to 30°; and
(e) a pore volume of pores having a pore radius within a range of 2000 to 20000 nm is 0.050 cc/g or less.

17 Claims, 2 Drawing Sheets

(56) References Cited

FOREIGN PATENT DOCUMENTS

| | | |
|---|---|---|
| EP | 0 697 247 A2 | 2/1996 |
| JP | 50-49233 | 5/1975 |
| JP | 61-21985 | 5/1986 |
| JP | 2-44771 | 10/1990 |
| JP | 4-217928 | 8/1992 |
| JP | 4-354541 | 12/1992 |
| JP | 5-64743 | 3/1993 |
| JP | 8-53678 | 2/1996 |
| JP | 10-52646 | 2/1998 |
| JP | 2002-537676 | 11/2002 |
| JP | 2005-169215 | 6/2005 |
| JP | 2005-520874 | 7/2005 |
| JP | 2005-232121 | 9/2005 |
| JP | 2006-8655 | 1/2006 |
| JP | 2006-16345 | 1/2006 |
| JP | 2007-191444 | 8/2007 |
| JP | 2007/291076 | 11/2007 |
| WO | WO96/13331 | 5/1996 |
| WO | WO00/10948 | 3/2000 |
| WO | WO 2005/097950 A1 | 10/2005 |
| WO | WO 2006/050487 A1 | 5/2006 |
| WO | WO 2007/083241 A2 | 7/2007 |
| WO | WO 2007/114195 A1 | 10/2007 |

* cited by examiner

PROPYLENE PRODUCTION PROCESS

CROSS REFERENCE TO RELATED APPLICATIONS

This application is a national phase application based on PCT/JP2008/066236, filed Sep. 9, 2008, which claims the priority of Japanese Patent Application Nos. 2007-241434, filed Sep. 18, 2007, and 2008-064843, filed Mar. 13, 2008, the content of all of which is incorporated herein by reference.

TECHNICAL FIELD

The present invention relates to a process for producing propylene from at least one of raw materials selected from the group consisting of ethylene and ethanol. In addition, the present invention relates to a catalyst containing a medium pore diameter zeolite and a production process of a catalyst containing a medium pore diameter zeolite.

BACKGROUND ART

For an example of a process for producing propylene, patent document 1 discloses propylene is produced by contacting a hydrocarbon raw material containing a high concentration of olefin with a crystalline silicate catalyst. Ethylene is added to the hydrocarbon raw material of the raw materials in this process.

Patent document 2 discloses a process for producing an aromatic compound by contacting a paraffin or olefin having 2 to 4 carbon atoms, or mixture thereof, with crystalline aluminosilicate zeolite.

Patent document 3 discloses a process for producing propylene using ethanol as a raw material that uses phosphate-based zeolite, while patent document 4 discloses a process for producing propylene using ethanol as a raw material that uses aluminosilicate composed of an 8-member or 9-member ring and having a pore diameter of less than 0.5 nm for the active component of a catalyst.

In addition, patent document 5 discloses a zeolite-containing catalyst composed of a zeolite, an aluminum phosphate-containing binder and a matrix, while patent document 6 discloses a zeolite-containing catalyst composed of a modified zeolite treated with a phosphate-containing aqueous solution and a matrix.

Patent document 1: U.S. Pat. No. 6,388,161
Patent document 2: Japanese Patent Laid-Open No. S50-49233
Patent document 3: Japanese Patent Application Laid-open No. 2007-191444
Patent document 4: Japanese Patent Application Laid-open No. 2007-291076
Patent document 5: Japanese Patent Application Laid-open No. H4-354541
Patent document 6: Japanese Patent Application Laid-open No. H5-64743

DISCLOSURE OF INVENTION

Problems to be Solved by the Invention

However, the processes disclosed in these documents are substantially processes that use a fixed bed reactor, while specific examples using a fluidized bed reactor are not described.

In addition, in the case of producing propylene from a raw material in the form of ethylene or ethanol using a fluidized bed reactor, stable operation is difficult due to a prominent decrease in the conversion over time due to the effects of fluidity and strength of the catalyst, adherence of carbonaceous compounds and the like.

The problems to be solved by the present invention is to provide a process for efficient and stable production of propylene from at least one of raw material selected from the group consisting of ethylene and ethanol using a fluidized bed reactor.

Means for Solving the Problems

The present inventors continuously made a diligent study for the purpose of solving the above-described problems, and consequently perfected the present invention by discovering that propylene can be produced efficiently and stably by contacting at least one of raw material selected from the group consisting of ethylene and ethanol and a specific catalyst containing a medium pore diameter zeolite within a fluidized bed reactor.

Specifically, the present invention provides a propylene production process, catalyst containing a medium pore diameter zeolite, and a production process of a catalyst containing a medium pore diameter zeolite as is indicated below:

[1] a process for producing propylene, comprising contacting at least one of raw materials selected from the group consisting of ethylene and ethanol with a catalyst containing a medium pore diameter zeolite in a fluidized bed reactor wherein,
the catalyst containing a medium pore diameter zeolite satisfies the following (a) through (e):
(a) a particle diameter of catalyst particles at 90% by weight or more is within a range of 10 to 197 μm,
(b) a bulk density of the catalyst particles is within a range of 0.7 to 1.1 g/cm$^3$,
(c) a mean compressive strength of the catalyst particles having a particle diameter within a range of 30 to 70 μm is 15 MPa or more, and a compressive strength of the catalyst particles at 90% by weight or more is 10 MPa or more,
(d) an angle of repose is 20 to 30°, and
(e) a pore volume of pores having a pore radius within a range of 2000 to 20000 nm is 0.050 cc/g or less;

[2] the process for producing propylene described in item [1], further comprising steps of:
separating propylene from exit gas of the fluidized bed reactor, and
recycling a portion or all of low boiling components containing ethylene in the exit gas and/or recycling a portion or all of high boiling components containing butene to the fluidized bed reactor;

[3] the process for producing propylene described in items [1] or [2], further comprising a step of: continuously or intermittently extracting a portion of the catalyst containing a medium pore diameter zeolite from the fluidized bed reactor, contacting the portion with gas containing oxygen, burning carbonaceous compounds adhered to the catalyst containing a medium pore diameter zeolite, and supplying the medium pore diameter zeolite to the fluidized bed reactor following burning;

[4] the process for producing propylene described in any one of items [1] to [3], wherein the catalyst containing the medium pore diameter zeolite contains a zeolite and a silica, and has a composition represented by the following formula (1):

$$\text{zeolite/silica} = 1/A \qquad (1)$$

(wherein A represents a ratio of a weight of the silica to a weight of the zeolite, and 0<A≤10), and is produced using a non-aggregating zeolite, in which a molar ratio of $SiO_2/Al_2O_3$ is 15 to 1000 and the mean particle diameter is 0.05 to 10 μm, and using a silica sol, in which a mean particle diameter of primary particles is 3 to 50 nm;

[5] the process for producing propylene described in any one of items [1] to [4], wherein the catalyst containing the medium pore diameter zeolite contains a zeolite, a silica and a phosphorous, and has a composition represented by the following formula (2):

$$zeolite/silica/phosphorous = 1/A/B \quad (2)$$

(wherein, A represents a ratio of a weight of the silica to a weight of the zeolite, B represents a ratio of a weight of elementary phosphorous to a total weight of the zeolite and the silica, 0<A≤10 and 0<B≤0.05), and is produced using a non-aggregating zeolite, in which a molar ratio of $SiO_2/Al_2O_3$ is 15 to 1000 and a mean particle diameter is 0.05 to 10 μm, and using a silica sol, in which a mean particle diameter of primary particles is 3 to 50 nm;

[6] the process for producing propylene described in any of items [1] to [5], wherein the catalyst containing the medium pore diameter zeolite contains at least one of element selected from the group of elements belonging to group IB of the periodic table;

[7] a catalyst containing a medium pore diameter zeolite, which satisfies the following (a) through (e):
(a) a particle diameter of catalyst particles at 90% by weight or more is within a range of 10 to 197 μm,
(b) a bulk density of the catalyst particles is within a range of 0.7 to 1.1 g/cm³,
(c) a mean compressive strength of the catalyst particles having a particle diameter within a range of 30 to 70 μm is 15 MPa or more, and a compressive strength of the catalyst particles at 90% by weight or more is 10 MPa or more,
(d) an angle of repose is 20 to 30°, and
(e) a pore volume of pores having a pore radius within a range of 2000 to 20000 nm is 0.050 cc/g or less;

[8] the catalyst containing the medium pore diameter zeolite described in item [7], wherein the catalyst contains a zeolite and a silica and has a composition represented by the following formula (1):

$$zeolite/silica = 1/A \quad (1)$$

(wherein A represents a ratio of a weight of the silica to the weight of the zeolite, and 0<A≤10), and
the zeolite is a non-aggregating zeolite, in which a molar ratio of $SiO_2/Al_2O_3$ is 15 to 1000 and a mean particle diameter is 0.05 to 10 μm;

[9] the catalyst containing the medium pore diameter zeolite described in items [7] or [8], wherein the catalyst contains a zeolite, a silica and a phosphorous, and has a composition represented by the following formula (2):

$$zeolite/silica/phosphorous = 1/A/B \quad (2)$$

(wherein A represents a ratio of a weight of the silica to a weight of the zeolite, B represents a ratio of a weight of the phosphorous to a total weight of the zeolite and the silica, 0<A≤10 and 0<B≤0.05), and
the zeolite is a non-aggregating zeolite, in which a molar ratio of $SiO_2/Al_2O_3$ is 15 to 1000 and a mean particle diameter is 0.05 to 10 μm;

[10] the catalyst containing the medium pore diameter zeolite described in any one of items [7] to [9], which contains at least one of element selected from the group of elements belonging to group IB of the periodic table;

[11] a process for producing a catalyst containing a medium pore diameter zeolite, the process comprising the steps of:
(i) preparing a raw material mixture by mixing a non-aggregating zeolite, in which a molar ratio of $SiO_2/Al_2O_3$ is 15 to 1000 and a mean particle diameter is 0.05 to 10 μm, and a silica sol, in which a mean particle diameter of primary particles is 3 to 50 nm, and
(ii) obtaining a dry powder by spray-drying the raw material mixture;

[12] a process for producing a catalyst containing a medium pore diameter zeolite, which comprises the steps of:
(i) preparing a raw material mixture by mixing a non-aggregating zeolite, in which a molar ratio of $SiO_2/Al_2O_3$ is 15 to 1000 and a mean particle diameter is 0.05 to 10 μm, a silica sol, in which a mean particle diameter of primary particles is 3 to 50 nm, and a phosphate compound, and
(ii) obtaining a dry powder by spray-drying the raw material mixture;

[13] the catalyst containing the medium pore diameter zeolite described in items [9] or [10], wherein the phosphorous is a water-soluble phosphorous compound; and,

[14] the catalyst containing the medium pore diameter zeolite described in items [9] or [10], wherein the phosphorous is phosphoric acid.

ADVANTAGEOUS EFFECTS OF THE INVENTION

According to the propylene production process of the present invention, propylene can be produced efficiently and stably from at least one of raw materials selected from the group consisting of ethylene and ethanol using a fluidized bed reactor, thereby making it extremely useful in terms of carrying out the process industrially.

BEST MODE FOR CARRYING OUT THE INVENTION

Hereinafter, the best mode for carrying out the present invention (hereinafter abbreviated as "the present embodiment") is described in detail. It is understood that the present invention is not limited to the following embodiment, and can be modified to be implemented within the scope of the gist thereof.

[1] Propylene Production Process

The propylene production process of the present embodiment is a process for producing propylene comprising contacting at least one of raw materials selected from the group consisting of ethylene and ethanol with a catalyst containing a medium pore diameter zeolite within a fluidized bed reactor, wherein
the catalyst containing the medium pore diameter zeolite satisfies the following (a) to (e):
(a) a particle diameter of 90% by weight or more of catalyst particles is within a range of 10 to 197 ™m, (b) a bulk density of the catalyst particles is within a range of 0.7 to 1.1 g/cm$^3$, (c) a mean compressive strength of catalyst particles having a particle diameter within a range of 30 to 70 μm is 15 MPa or more, and a compressive strength of 90% by weight or more of the catalyst particles is 10 MPa or more, (d) an angle of repose is 20 to 30°, and (e) a pore volume of pores having a pore radius within a range of 2000 to 20000 nm is 0.050 cc/g or less.

(1) Raw Material

In the present embodiment, the raw material used in the propylene production process is at least one of raw materials selected from the group consisting of ethylene and ethanol.

In the case of using ethylene for the raw material, there are no particular limitations on the ethylene content based on hydrocarbon compounds contained in the raw material. From the viewpoint of productivity, the ethylene content is preferably 20% by weight or more, more preferably 30% by weight or more and even more preferably 50% by weight or more.

In the case of using ethanol for the raw material, there are no particular limitations on the ethanol content as ethylene based on hydrocarbon compounds contained in the raw material. From the viewpoint of productivity, the ethanol content as ethylene is preferably 20% by weight or more, more preferably 30% by weight or more and even more preferably 50% by weight or more.

In the case of using raw materials containing both ethylene and ethanol for the raw materials, there are no particular limitations on the ratio of ethylene and ethanol, and ethylene and ethanol can be supplied at an arbitrary ratio. In this case as well, the value as ethylene is used for the ethanol, and there are no particular limitations on the total content of ethylene and ethanol as ethylene based on the hydrocarbon compounds contained in the raw materials. From the viewpoint of productivity, the total content of ethylene and ethanol as ethylene is preferably 20% by weight or more, more preferably 30% by weight or more and even more preferably 50% by weight or more.

Ethylene obtained by thermal decomposition and/or oxidative dehydrogenation of ethane or ethylene obtained by dehydration of biomass ethanol, for example, can be used for the ethylene. In addition, ethylene obtained by thermal decomposition of ethane in the presence of water vapor can also be used. Ethylene obtained by thermal decomposition or catalytic decomposition of naphtha or ethylene obtained by dehydration of industrially produced ethanol can also be used.

Although there are no particular limitations on the supply source of the ethanol, biomass-derived ethanol or petroleum-derived ethanol, for example, can be used.

An example of biomass ethanol includes ethanol obtained from plant resources, and although there are no particular limitations thereon, specific examples include ethanol obtained by fermentation of cane sugar or corn, ethanol obtained from woody resources such as waste wood, thinned wood, rice straw or agricultural products, and the like. In addition, although industrially produced ethanol can also be used, the use of biomass ethanol is preferable from the viewpoint of carbon neutrality.

Alkanes or olefins and the like may also be contained in the raw materials in addition to ethylene and/or ethanol.

Examples of alkanes include methane, ethane, propane, butane, pentane, hexane, heptane, octane and nonane.

Examples of olefins include propylene, butene, pentene, hexene, heptene, octene and nonene.

Cycloalkanes such as cyclopentane, methylcyclopentane or cyclohexane; cycloolefins such as cyclopentene, methyl-cyclopentene, or cyclohexene; dienes such as cyclohexadiene, butadiene, pentadiene or cyclopentadiene; and/or acetylenes such as acetylene or methylacetylene may also be contained in the raw materials. Hydrocarbon compounds such as t-butyl alcohol, methyl t-butyl ether, diethyl ether, methyl ethyl ether, dimethyl ether or methanol may also be contained in the raw materials. Water, hydrogen, nitrogen, carbon dioxide and carbon monoxide may also be contained in the raw materials.

(2) Production Process

In the present embodiment, propylene can be produced by supplying raw materials to a fluidized bed reactor containing a catalyst containing a medium pore diameter zeolite of the present embodiment to be described later and contacting the catalyst and raw materials to convert ethylene and/or ethanol in the raw materials.

(2-1) Water Vapor Treatment

A catalyst containing a medium pore diameter zeolite can be pretreated under conditions of a water vapor partial pressure of 0.01 atm or more at a temperature of 300 to 900° C. prior to starting an ethylene and/or ethanol conversion reaction. Oxygen, nitrogen and the like can be contained as gas components other than water vapor during heat treatment in the presence of water vapor.

The use of a catalyst containing a medium pore diameter zeolite that has undergone pretreatment in a propylene production process makes it possible to inhibit deterioration caused by coking, thereby allowing the propylene yield to be improved.

(2-2) Reaction Conditions

In a propylene production process of the present embodiment, the reaction temperature is preferably within a range of 400 to 650° C. and more preferably within a range of 500 to 600° C. The reaction pressure is preferably within a range of 0.01 to 3 MPa and more preferably within a range of 0.05 to 1 MPa.

The supply rate of ethylene and/or ethanol is preferably 0.05 to 20 and more preferably 0.1 to 10 Hr$^{-1}$ in terms of the weight hourly space velocity (WHSV) based on the weight of the catalyst containing the medium pore diameter zeolite.

In the present embodiment, by controlling the actual gas flow rate in the fluidized bed reactor under these conditions to preferably within a range of 0.1 to 1.0 m/sec, more preferably within a range of 0.2 to 0.9 m/sec and even more preferably within a range of 0.3 to 0.8 m/sec, propylene can be produced efficiently and stably.

In the present embodiment, WHSV can be determined according to the following calculation formula:

WHSV (1/Hr)=total amount of hydrocarbon compounds and H$_2$ in feed gas (g/hr)/amount of the catalyst containing the medium pore diameter zeolite (g)

However, in the case of using ethanol for the raw material, the amount of hydrocarbon compounds was calculated by converting ethanol to ethylene by dehydration.

(2-3) Fluidized Bed Reactor

In the present embodiment, a fluidized bed reactor is used for the reactor for contacting and reacting ethylene and/or ethanol with a catalyst containing a medium pore diameter zeolite.

Although a fluid bed reactor and a riser reactor can be used for the fluidized bed reactor, the fluid bed reactor can be used preferably from the viewpoint of efficient and stable production of propylene.

An example of the structure of the fluid bed reactor includes a reactor having a gas dispersion tube for supplying a raw material gas in the bottom of the reactor and/or lower portion of the reactor, having a cooling coil for removing heat in the thick layer and thin layer of the catalyst as necessary, and having a cyclone for separating reaction gas and catalyst in the upper portion of the reactor. In addition, a cyclone can also be provided outside the reactor.

(2-4) Ethylene Conversion and Propylene Yield

In the present embodiment, the ethylene conversion and propylene yield can be determined according to the following formulas (3) and (4), respectively, by analyzing the product using a gas chromatograph in which TCD-FID are connected in series.

Ethylene conversion=[(wt % of ethylene in gas supplied to inlet of fluidized bed reactor)−(wt % of ethylene in gas discharged from outlet of fluidized bed reactor)]/(wt % of ethylene in gas supplied to inlet of fluidized bed reactor)×100   Formula (3)

Propylene yield=[(wt % of propylene in gas discharged from outlet of fluidized bed reactor)−(wt % of propylene in gas supplied to inlet of fluidized bed reactor)]/(wt % of ethylene in gas supplied to inlet of fluidized bed reactor)×100   Formula (4)

Since ethylene is formed by a dehydration reaction in the reactor even if ethanol is used for a raw material, the ethanol conversion rate can be calculated in the same manner by converting the ethanol in the feed gas to a wt % of ethylene.

(3) Recycling of Raw Materials

The propylene production process of the present embodiment is preferably a propylene production process further comprising the steps of:

separating propylene from gas discharged from the fluidized bed reactor, and recycling a portion or all of low boiling components containing ethylene in the exit gas and/or recycling a portion or all of high boiling components containing butene to the fluidized bed reactor.

Distillative separation and the like can be used to separate propylene from the exit gas of the fluidized bed reactor.

Recycling of a portion or all of low boiling components containing ethylene and/or a portion or all of high boiling components containing butene to the fluidized bed reactor following separation of propylene from the exit gas is an extremely effective method for efficiently producing propylene.

There are no particular limitations on the recycled amounts of low boiling components containing ethylene and high boiling components containing butene, and since these amounts can be changed corresponding to the amount of propylene produced, they are able to impart flexibility to the amount of propylene produced.

(4) Regeneration of Catalyst Containing Medium Pore Diameter Zeolite

The propylene production process of the present embodiment is preferably a propylene production process further comprising a step of: continuously or intermittently extracting a portion of a catalyst containing a medium pore diameter zeolite from the fluidized bed reactor, contacting with gas containing oxygen, burning carbonaceous compounds adhered to the catalyst containing the medium pore diameter zeolite, and supplying the a catalyst containing a medium pore diameter zeolite to the fluidized bed reactor following burning.

In the present embodiment, the reactivity of the catalyst containing the medium pore diameter zeolite decreases as the reaction continues due to adherence of carbonaceous compounds referred to as coke. Continuously or intermittently extracting a portion of this catalyst having decreased activity from the fluidized bed reactor and burning carbonaceous compounds adhered to the catalyst containing the medium pore diameter zeolite using gas containing oxygen followed by recycling to the fluidized bed reactor is an extremely effective method for stable production of propylene.

Although a fluidized calcining furnace, rotary furnace, tunnel furnace, tubular furnace or muffle furnace and the like can be used to burn carbonaceous compounds adhered to a catalyst containing a medium pore diameter zeolite, a fluidized calcining furnace is used preferably in order to efficiently carry out the extraction, regeneration and recycling steps for this catalyst.

A furnace having a structure similar to that of the fluidized bed reactor can be used for the fluidized calcining furnace, and a cooling coil can also be enhanced for efficiently removing heat of burning. The temperature for burning carbonaceous compounds adhered to the catalyst containing the medium pore diameter zeolite is preferably within the range of 400 to 800° C. and more preferably within the range of 500 to 700° C. Gas containing oxygen at 0.1 to 30 vol % is preferably used for the feed gas, while that containing oxygen at 1 to 21 vol % is used more preferably.

Specific examples of gas containing oxygen include air and air mixed with oxygen or diluting gas.

Although nitrogen or carbon dioxide is used preferably for the diluting gas, water vapor, carbon monoxide, hydrocarbon compounds or hydrogen and the like can also be used.

The pressure of the feed gas containing oxygen is preferably within the range of 0.05 to 1.0 MPa and more preferably within the range of 0.1 to 0.5 MPa.

Burning treatment for regenerating catalyst containing a medium pore diameter zeolite can be carried out by setting conditions such that 80% by weight or more, and preferably 90% by weight or more, of carbonaceous compounds adhered to the catalyst can be removed.

[2] Catalyst Containing Medium Pore Diameter Zeolite

The catalyst containing the medium pore diameter zeolite used in the present embodiment is a catalyst containing a medium pore diameter zeolite that satisfies the following (a) to (e):

(a) a particle diameter of 90% by weight or more of catalyst particles is within a range of 10 to 197 μm, (b) a bulk density of catalyst particles is within a range of 0.7 to 1.1 g/cm³, (c) a mean compressive strength of catalyst particles having a particle diameter within a range of 30 to 70 μm is 15 MPa or more, and a compressive strength of 90% by weight or more of catalyst particles is 10 MPa or more, (d) an angle of repose is 20 to 30°, and (e) a pore volume of pores having a pore radius within a range of 2000 to 20000 nm is 0.050 cc/g or less.

In the present embodiment, the term "a medium pore diameter zeolite" refers to "zeolite in which the range of pore diameter is intermediate to the pore diameter of small pore diameter zeolite as represented by A-type zeolite and the pore diameter of large pore diameter zeolite as represented by mordenite, X-type zeolite and Y-type zeolite".

In the present embodiment, the zeolite contained in the catalyst containing the medium pore diameter zeolite refers to crystalline aluminosilicate having an intermediate pore diameter, and is equivalent to zeolite having a pore diameter of 0.5 to 0.65 nm.

The medium pore diameter zeolite has a so-called oxygen 10-member ring in the crystal structure thereof. There are no particular limitations on the medium pore diameter zeolite, and examples include ZSM-5 and so-called pentasil-type zeolites having a structure similar to ZSM-5. Namely, examples of such zeolites include ZSM-5, ZSM-8, ZSM-11, ZSM-12, ZSM-18, ZSM-23, ZSM-35 and ZSM-39. Preferable examples of zeolites include those of a framework structure type in accordance with IUPAC recommendations as represented by an MFI structure, a specific example of which is ZSM-5. These zeolites can also be used as proton types.

(a) to (c) Particle Diameter, Bulk Density and Compressive Strength of Catalyst Particles The catalyst containing the medium pore diameter zeolite in the present embodiment is a catalyst containing a medium pore diameter zeolite in which a particle diameter of 90% by weight or more of catalyst particles is within a range of 10 to 197 μm from the viewpoint of fluidity.

The particle diameter of 95% by weight or more of the catalyst particles is preferably within the range of 15 to 150

The catalyst containing the medium pore diameter zeolite in the present embodiment is a catalyst containing a medium pore diameter zeolite in which a bulk density of catalyst particles is within a range of 0.7 to 1.1 $g/cm^3$ from the viewpoint of maintaining a satisfactory fluid state. The bulk density of the catalyst particles is preferably within the range of 0.8 to 1.0 $g/cm^3$.

The catalyst containing the medium pore diameter zeolite in the present embodiment is a catalyst containing a medium pore diameter zeolite in which a mean compressive strength of catalyst particles having a particle diameter within a range of 30 to 70 μm is 15 MPa or more, and a compressive strength of 90% by weight or more of the catalyst particles is 10 MPa or more from the viewpoint of reducing catalyst loss.

(d) Angle of Repose

The catalyst containing the medium pore diameter zeolite in the present embodiment is a catalyst containing a medium pore diameter zeolite in which an angle of repose is 20 to 30°. If the angle of repose is smaller than 20°, fluidity becomes excessive thereby tending to make handling poor. If the angle of repose exceeds 30°, fluidity decreases thereby tending to result in increased susceptibility to the occurrence of bridging between particles.

(e) Pore Volume

The catalyst containing the medium pore diameter zeolite in the present embodiment is a catalyst containing a medium pore diameter zeolite in which a pore volume of pores having a pore radius within a range of 2000 to 20000 nm is 0.050 cc/g or less. The pore volume of pores having the pore radius within the range of 2000 to 20000 nm is preferably 0.040 cc/g or less and more preferably 0.030 cc/g or less. If the pore volume of pores having the pore radius of 2000 to 20000 nm exceeds 0.050 cc/g, attrition loss of the catalyst increases.

As a result of satisfying the conditions of (a) to (e) as described above, the catalyst containing the medium pore diameter zeolite in the present embodiment, the attrition loss of the catalyst containing the medium pore diameter zeolite as represented by formula (5) below can be made to be 3% by weight or less, thereby achieving a reduction in catalyst loss for carrying out industrially.

Formula (5):

$$\text{Attrition loss (wt \%)} = D/(E-C) \times 100 \quad (5)$$

(In the formula, C represents the weight (g) of catalyst particles lost in 0 to 5 hours, D represents the weight (g) of catalyst particles lost in 5 to 20 hours, and E represents the weight (g) of catalyst particles used in the test.)

If the attrition loss of catalyst particles is 3% by weight or less, the catalyst particles have extremely low levels of attrition and damage and superior mechanical strength, thereby enabling them to be preferably used as a catalyst for a fluidized bed reaction.

There are no particular limitations on the binder used to prepare the catalyst containing the medium pore diameter zeolite in the present invention, and examples of binders that can be used include silica, alumina and kaolin, and these binders can be used alone or as a mixture.

In the case of containing a zeolite and a silica, a catalyst containing a medium pore diameter zeolite that has a composition represented by the following formula (1):

$$\text{zeolite/silica} = 1/A \quad (1)$$

(wherein A represents a ratio of a weight of the silica to a weight of the zeolite, and $0 < A \le 10$), and is produced using a non-aggregating zeolite, in which a molar ratio $SiO_2/Al_2O_3$ is 15 to 1000 and a mean particle diameter is 0.05 to 10 μm, for a raw material of the catalyst and using a silica sol, in which a mean particle diameter of primary particles is 3 to 50 nm, for a raw material of the catalyst, is preferable for the catalyst containing the medium pore diameter zeolite used in the present embodiment.

In the case of containing a zeolite, a silica and a phosphorous, a catalyst containing a medium pore diameter zeolite that has a composition represented by the following formula (2):

$$\text{zeolite/silica/phosphorous} = 1/A/B \quad (2)$$

(wherein, A represents a ratio of a weight of the silica to a weight of the zeolite, B represents a ratio of a weight of elementary phosphorous to a total weight of the zeolite and the silica, $0 < A \le 10$ and $0 < B \le 0.05$), and is produced using a non-aggregating zeolite, in which a molar ratio of $SiO_2/Al_2O_3$ is 15 to 1000 and a mean particle diameter is 0.05 to 10 μm, for a raw material of the catalyst and using a silica sol, in which a mean particle diameter of primary particles is 3 to 50 nm, for a raw material of the catalyst, is preferable for the catalyst containing the medium pore diameter zeolite used in the present embodiment.

The zeolite contained in the catalyst containing the medium pore diameter zeolite in the present embodiment is a zeolite in which a molar ratio of $SiO_2/Al_2O_3$ is preferably within a range of 15 to 1000 for a raw material thereof, more preferably within a range of 20 to 500, and even more preferably within a range of 20 to 300 from the viewpoint of reactivity.

The zeolite contained in the catalyst containing the medium pore diameter zeolite in the present embodiment is preferably a non-aggregating zeolite in which the mean particle diameter is 0.05 to 10 μm for a raw material thereof.

Normally, fine primary particles of zeolite aggregate during hydrothermal synthesis to form secondary particles several to 20 μm in diameter.

Examples of methods of obtaining "non-aggregating zeolite" include a method for de-aggregating zeolite to a mean particle diameter within a range of 0.05 to 10 μm by breaking up aggregates thereof by subjecting aggregating zeolite to mechanical dispersion treatment such as de-aggregating, impacting or shearing, or to chemical treatment such as dissolving with an alkaline solution, and a method in which zeolite is synthesized to a mean particle diameter of 0.05 to 10 μm.

In the case the zeolite used as a raw material forms aggregates, the zeolite can be used in the form of a non-aggregating zeolite by mechanically de-aggregating using a jet mill and the like. Instead of de-aggregating with an easily used ball mill, it is preferable to use a jet mill whereby de-aggregating treatment is carried out by ultra-high-speed jetting of highly compressed air or high-pressure steam.

An example of a method of synthesizing zeolite so as to have a mean particle diameter of 0.05 to 10 μm includes hydrothermal synthesis using a seed slurry as described in Japanese Patent Application Laid-open No. H10-52646. According to this publication, the seed slurry is obtained by the following steps: adding an aqueous solution containing aluminium sulfate, 1,3-dimethylurea and sulfuric acid to sodium silicate to obtain a homogeneous gel; heating the resulting gel while stirring in an autoclave; mixing: filtering the resulting slurry, then washing with water, drying, and calcining: mixing the resulting Na-type ZSM-5 powder with sodium silicate, $Al_2(SO_4)_3$ and sulfuric acid; stirring the resulting mixture under pressurizing and heating. The resulting seed slurry from these procedure is then crystallized while stirring with sodium silicate, $Al_2(SO_4)_3$ and sulfuric acid under heating and pressurizing to obtain the zeolite. Although it is necessary to set the heating, pressurization and stirring conditions to suitable values in order to obtain non-aggregating zeolite, these conditions can be determined by a person with ordinary skill in the art by referring to the description of Japanese Patent Application Laid-open No. H10-52646.

The use of zeolite in the production of the catalyst containing the medium pore diameter zeolite while in the state of "non-aggregating zeolite" allows the obtaining of a fluidized bed catalyst having superior physical properties such as shape and strength. In addition, the addition of a phosphorous compound makes it possible to further improve performance.

In the present embodiment, "non-aggregating" refers to the percentage of 100 zeolite primary particles as observed with an electron microscope (SEM) that are partially bound to other primary particles being 50% or less. The mean particle diameter of the non-aggregating zeolite is preferably 0.05 to 10 μm, more preferably 0.5 to 5 μm and even more preferably 0.5 to 4 μm.

In the present embodiment, the mean particle diameter of zeolite refers to a value measured with a laser diffraction/scattering particle size distribution analyzer. In addition, observation of particle shape can be carried out with an electron microscope (SEM).

The mean particle diameter of the zeolite contained in the catalyst containing the medium pore diameter zeolite is preferably 0.05 to 10 μm, more preferably 0.5 to 5 μm and even more preferably 0.5 to 4 μm.

If the mean particle diameter of the zeolite exceeds 10 μm, the compressive strength of the catalyst particles decreases tending to cause an increase in attrition loss. If the mean particle diameter of the zeolite is less than 0.05 μm, the crystallinity of the zeolite decreases tending to cause a decrease in reactivity when used as a catalyst for a fluidized bed reaction.

Metaloaluminosilicates, in which a portion of an aluminum atoms that compose a crystalline aluminosilicate are substituted with elements such as Ga, Fe, B and/or Cr, or metalosilicates, in which all of an aluminum atoms that compose a crystalline aluminosilicate are substituted with elements indicated above, can be used for a catalyst containing a medium pore diameter zeolite.

The silica used in the catalyst containing the medium pore diameter zeolite in the present embodiment preferably uses as a raw material thereof a silica sol in which a mean particle diameter of primary particles is 3 to 50 nm.

In the present embodiment, "silica" refers to silica contained in a silica sol used to produce the catalyst containing the medium pore diameter zeolite, and with the exception of cases in which specifically stated otherwise, does not refer to silica that composes zeolite in the form of crystalline aluminosilicate.

The mean particle diameter of the silica primary particles in the silica sol is extremely intimately related to the attrition resistance and bulk density of silica molded articles. If the mean particle diameter is within the range of 3 to 50 nm, the contact surface area with the zeolite particles increases, thereby making a packed state of zeolite particles and silica more homogeneous and dense. Consequently, attrition resistance of silica molded articles improves, and bulk density also tends to increase. The mean particle diameter of the silica primary particles is preferably 3 to 30 nm and more preferably 3 to 20 nm. In addition, a silica sol having a broad silica primary particle size distribution can be used, by mixing with several species of silica colloids having different particle diameters in which a mean particle diameter is 50 nm or less.

Examples of silica sols that can be used include alkaline silica sols or acidic silica sols stabilized with ammonium ions or sodium ions, silica sols stabilized with amines, and the like. Silica sols stabilized with ammonium ions are preferable. The silica sol can also be used with aluminosilicate, alumina, titania, zirconia, kaolin or diatomaceous earth and the like, and two or more species thereof can also be used in combination.

Examples of phosphorous compounds used in the catalyst containing the medium pore diameter zeolite in the present embodiment include phosphoric acid, phosphorous acid, hypophosphorous acid, pyrophosphoric acid, polyphosphoric acid, ammonium monohydrogen phosphate, ammonium dihydrogen phosphate, triammonium phosphate, ammonium perphosphate, ammonium hypophosphite, phosphorous pentoxide and phosphines.

From the viewpoint of the strength of the catalyst containing the medium pore diameter zeolite, water-soluble phosphorous compounds such as phosphoric acid, ammonium monohydrogen phosphate, ammonium dihydrogen phosphate, triammonium phosphate, pyrophosphoric acid or polyphosphoric acid are preferable, while phosphoric acid is more preferable. These can be used alone, as a mixture or as an aqueous solution.

In the present embodiment, in the above-mentioned formulas (1) and (2) representing the composition of the catalyst containing the medium pore diameter zeolite, A, which represents the weight ratio of silica to the weight of zeolite, is preferably $0 < A \leq 10$, more preferably $0.1 \leq A \leq 10$ and even more preferably $0.5 \leq A \leq 5$.

If A is greater than 10, the shape of the catalyst containing the medium pore diameter zeolite becomes poor, which tends to lower fluidity. In addition, if A is greater than 10 in the case of using the catalyst containing the medium pore diameter zeolite as a catalyst for a fluidized bed reaction, reactivity tends to decrease since an adequate amount of zeolite is not contained in the catalyst containing the medium pore diameter zeolite.

In the present embodiment, in the above-mentioned formula (2) representing the composition of the catalyst containing the medium pore diameter zeolite, B, which represents the weight ratio of elementary phosphorous to the total weight of zeolite and silica, is preferably $0 < B \leq 0.05$, more preferably $0.001 \leq B \leq 0.05$ and even more preferably $0.005 \leq B \leq 0.04$.

Although the presence of phosphorous has the tendency to increase the strength of the catalyst containing the medium pore diameter zeolite, if B exceeds 0.05, problems occur in the shape and reactivity of the catalyst containing the medium pore diameter zeolite.

The weight ratio of zeolite/silica in the catalyst containing the medium pore diameter zeolite can be measured in the manner described below in the case it is unknown.

A sample of a standard mixture of a medium pore diameter zeolite and a silica mixed in an arbitrary ratio is prepared, and its powder X-ray diffraction intensity is determined in advance. X-ray intensity is then measured for a sample in which a weight ratio of zeolite/silica is unknown under the same conditions, and the weight ratio of zeolite/silica in the catalyst containing the medium pore diameter zeolite can be determined from a comparison (intensity comparison) with the X-ray diffraction intensity of the zeolite-containing catalyst. The medium pore diameter zeolite used for the standard mixture sample is preferably that for which the powder X-ray diffraction pattern is identical or similar to the powder X-ray diffraction pattern for the zeolite of the catalyst containing the medium pore diameter zeolite to be measured. For example, the weight ratio of zeolite/silica can be determined by using a powder X-ray diffraction system (RINT, Rigaku Corp.) for the measuring instrument, and measuring X-ray intensity under measuring conditions consisting of the use of a Cu cathode, tube voltage of 40 kV, tube current of 30 mA and scanning speed of 1 deg/min.

The molar ratio of $SiO_2/Al_2O_3$ of the zeolite in the catalyst containing the medium pore diameter zeolite can be measured in the manner described below in the case it is unknown.

After embedding the catalyst containing the medium pore diameter zeolite in polyester resin, the resin is ground to expose a cross-sectional surface of the catalyst. This particle cross-section is then observed with an electron microscope provided with an energy-dispersive X-ray spectrometer (EDX) followed by measurement of the content of Si and Al in the zeolite portion thereby enabling determination of the molar ratio of $SiO_2/Al_2O_3$. For example, the molar ratio of $SiO_2/Al_2O_3$ can be determined by using an electron microscope with EDX (S-800, Hitachi, Ltd.) for the electron microscope provided with EDX and measuring the contents of Si and Al under measuring conditions consisting of a sample current of $3 \times 10^{-10}$ A and acceleration voltage of 20 kV.

As will be described later, in the case of preparing the catalyst containing the medium pore diameter zeolite, the weight ratio of zeolite/silica and the molar ratio of $SiO_2/Al_2O_3$ for zeolite in the catalyst containing the medium pore diameter zeolite generally maintain the charged composition regardless of the presence or absence of a calcining step.

The catalyst containing the medium pore diameter zeolite used in the present embodiment is preferably a catalyst containing a medium pore diameter zeolite which, in the case of containing a zeolite and a silica, has a composition represented by the following formula (1):

zeolite/silica=1/$A$ (1)

(wherein A represents a ratio of a weight of the silica to a weight of the zeolite, and 0<A≤10), and the zeolite is a non-aggregating zeolite in which a molar ratio of $SiO_2/Al_2O_3$ is 15 to 1000 and a mean particle diameter is 0.05 to 10 μm.

The catalyst containing the medium pore diameter zeolite used in the present embodiment is preferably a catalyst containing a medium pore diameter zeolite which, in the case of containing a zeolite, a silica and a phosphorous, has a composition represented by the following formula (2):

zeolite/silica/phosphorous=1/$A$/$B$ (2)

(wherein A represents a ratio of a weight of the silica to a weight of the zeolite, B represents a ratio of a weight of elementary phosphorous to a total weight of the zeolite and the silica, 0<A≤10 and 0<B≤0.05), and the zeolite is a non-aggregating zeolite in which a molar ratio of $SiO_2/Al_2O_3$ is 15 to 1000 and a mean particle diameter is 0.05 to 10 μm.

[3] Production Process of Catalyst Containing Medium Pore Diameter Zeolite

Examples of a production process of the catalyst containing the medium pore diameter zeolite in the present embodiment include:

(I) a method comprising the steps of:
(i) preparing a raw material mixture by mixing a non-aggregating zeolite, in which a molar ratio of $SiO_2/Al_2O_3$ is 15 to 1000 and a mean particle diameter is 0.05 to 10 μm, and a silica sol in which a mean particle diameter of primary particles is 3 to 50 nm, and
(ii) spray-drying the raw material mixture to obtain a dry powder; and (II) a method comprising the steps of:
(i) preparing a raw material mixture by mixing a non-aggregating zeolite, in which a molar ratio of $SiO_2/Al_2O_3$ is 15 to 1000 and a mean particle diameter is 0.05 to 10 μm, a silica sol in which a mean particle diameter of primary particles is 3 to 50 nm, and a phosphorous compound, and
(ii) spray-drying the raw material mixture to obtain a dry powder.

Since the process of (I) and the process of (II) share common characteristics with the exception of whether or not the raw material mixture contains a phosphorous compound, both processes are explained together. A catalyst containing a medium pore diameter zeolite can be produced by each process by referring to the previously described raw material compounds and composite ratio of the raw material mixture.

The use of the non-aggregating zeolite, in which the molar ratio of $SiO_2/Al_2O_3$ is 15 to 1000 and the mean particle diameter is 0.05 to 10 μm, and the silica sol in which the mean particle diameter of silica primary particles is 3 to 50 nm for raw materials, allows the obtaining of a catalyst containing a medium pore diameter zeolite that has particularly superior mechanical strength. Contact between zeolite and silica sol in the raw material composition is favorable as a result of combining these raw materials, and as a result, the packed state of the zeolite and the silica is presumed to be homogeneous and dense. Thus, the mixed state of the zeolite and the silica sol in the raw material mixture is important for expressing mechanical strength of the catalyst containing the medium pore diameter zeolite, and the mixing of the zeolite in a non-aggregated state is particularly important.

Zeolite can be used in the form of zeolite powder, a slurry in which zeolite is dispersed or suspended in water, a slurry in which zeolite is dispersed or suspended in a portion of a silica sol used as a raw material, or a slurry in which zeolite is dispersed or suspended in an aqueous solution of a phosphorous compound, and is preferably used in the form of zeolite powder, slurry in which zeolite is dispersed or suspended in water, or slurry in which zeolite is dispersed or suspended in a portion of a silica sol used as a raw material.

(i) Step for Preparing Raw Material Mixture

Step (i) of the production process of the catalyst containing the medium pore diameter zeolite in the present embodiment is a step for producing a raw material mixture by mixing (I) a zeolite and a silica sol or (II) a zeolite, a silica sol and a phosphorous compound.

There are no particular limitations on the order in which (I) the zeolite and the silica sol are mixed, and the order in which (II) the zeolite, the silica sol and the phosphorous compound are mixed.

In the case of (I), zeolite may be added to silica sol or silica sol may be added to zeolite. In the case of (II), zeolite may be added to silica sol followed by the addition of phosphorous compound to the mixture thereof, or phosphorous compound may be added to silica sol followed by the addition of zeolite to the mixture thereof. In either processes of (I) or (II), the zeolite is preferably used in the form of zeolite powder, slurry in which zeolite is dispersed or suspended in water, or slurry in which zeolite is dispersed or suspended in a portion of the silica sol used as a raw material. The phosphorous compound may be used as is or may be used after dispersing in water and the like.

Acid may be suitably added to the raw material composition of the catalyst containing the medium pore diameter zeolite to preferably adjust the pH of the raw material mixture. In this case, examples of acids used include sulfuric acid, hydrochloric acid and nitric acid, and nitric acid is used preferably. The pH of the raw material mixture is preferably 0.5 to 10 and more preferably 0.5 to 4.

Zeolite and silica are contained in the raw material mixture in the form of a solid fraction. The weight concentration of the solid fraction of the raw material mixture is preferably 5 to 70% by weight and more preferably 10 to 50% by weight. Water may also be suitably added to the raw material mixture to adjust the weight concentration of the solid fraction.

A surfactant may also be added to adjust the surface tension of the raw material mixture for the purpose of making the shape of the catalyst containing the medium pore diameter zeolite more spherical.

The stirring time of the raw material mixture is preferably 0.5 to 50 hours and more preferably 1 to 5 hours. The temperature of the mixture during stirring is preferably 10 to 90° C., more preferably 15 to 70° C. and even more preferably 15 to 40° C. The viscosity of the raw material mixture may be increased by heating as necessary.

(ii) Step for Obtaining Dry Powder

Step (ii) is a step for obtaining a dry powder by spray-drying the raw material mixture obtained in step (i). The raw material mixture may be spray-dried immediately after preparation, or the raw material mixture may be spray-dried after mixing and stirring for a long period of time to control the amount of the raw material mixture adsorbed onto the zeolite following preparation. Although an ordinary industrial use method such as a rotating disc system, dual fluid nozzle system or high-pressure nozzle system may be employed for spraying the raw material mixture, a rotating disc system is particularly preferable. Steam or air heated with an electrical heater and the like is preferably used for the drying heat source. The temperature at the dryer inlet is preferably 100 to 400° C. and more preferably 150 to 300° C. The temperature at the dryer outlet is preferably 80 to 170° C. and more preferably 90 to 150° C.

The production process of the present embodiment may further comprise a step (iii) as necessary for the purpose of obtaining a catalyst containing a medium pore diameter zeolite having higher attrition resistance. This step (iii) is a step for calcining the dry powder obtained in step (ii).

Calcining of the dry powder can be carried out using a muffle furnace, rotary furnace, tunnel furnace, tubular furnace or fluidized calcining furnace and the like. The calcining temperature is preferably 500 to 900° C., more preferably 550 to 850° C. and even more preferably 600 to 700° C. The calcining time is preferably 0.5 to 8 hours and more preferably 1 to 5 hours.

The calcining step can be carried out in an atmospheric atmosphere, inert atmosphere or in a vacuum. In addition, the calcining step may be repeated. Following calcining, surplus phosphorous components in the catalyst containing the medium pore diameter zeolite can be rinsed with water or hot water.

In the case of granulating after spray-drying a slurry as in the prior art, powder particles may be destroyed or become weakened due to the appearance of openings of the particle surfaces, collapsing of the surface or the shape becoming irregular due to the following mechanism: 1) shrinkage of slurry droplets and solidification of the surface of slurry droplets begin by evaporation from the slurry droplets 2) destruction (cracking, chipping) of powder particles or the appearance of openings of the surfaces thereof occurs as a result of rising of the internal pressure in powder particles, and 3) internal pressure of the particles is either eliminated or changes to negative pressure causing the surfaces of the powder particles to collapse when the temperature of the powder particles subsequently lowers to room temperature.

Since the catalyst containing the medium pore diameter zeolite of the present embodiment contains a non-aggregating zeolite, the surface area over which the zeolite contacts silica particles of the silica sol is large, and this is presumed to result in the effect of improving the strength of the zeolite-containing catalyst.

Moreover, in the case of the catalyst containing the medium pore diameter zeolite that contains phosphorous, although the details are unknown, the phosphorous compound exerts some form of catalytic action on the silica particles, and this is presumed to allow the obtaining of spherical powder particles having a smooth surface as a result of 1) the silica particles being crosslinked by dehydration and condensation of silanol groups (SiOH), 2) a silica layer being formed on the surface layers of liquid droplets during spray drying, and 3) destruction and the appearance of openings of the powder particles accompanying increases in internal pressure as well as collapse of the powder particles due to decreases in internal pressure or the formation of negative pressure being inhibited. In particular, the use of a silica sol having a comparative small mean particle diameter increases the contact surface area between silica sol particles, which is thought to make the crosslinked structure between silica particles stronger. In addition, improvement in attrition resistance is attributable to not only the crosslinked structures formed between silica particles, but also to the zeolite and silica being packed more homogeneously and densely in the dry powder as previously described. In addition, the phosphorous compound also acts to promote sintering between silica sol particles as a result of calcining, and this is presumed to further contribute to improvement of attrition resistance.

In the present embodiment, the catalyst containing the medium pore diameter zeolite preferably contains at least one of metal element selected from the group consisting of metal elements belonging to group IB of the periodic table, and means that the zeolite is contained in the state of cations corresponding to the group IB metal or those cations are loaded onto the catalyst.

The containing of at least one of metal selected from the group consisting of metals belonging to group IB of the periodic table, such as copper, silver or gold, by the catalyst containing the medium pore diameter zeolite is one preferable aspect of the present embodiment. More preferable examples of group IB metals include copper and silver, while silver is even more preferable.

The "periodic table" in the present embodiment refers to the periodic table described on pages 1 to 15 of the CRC Handbook of Chemistry and Physics, 75th edition, David R. Lide, et al. editors, published by CRS Press Inc. (1994-1995).

An example of a method for containing at least one of metal element selected from the group consisting of metal elements belong to group IB of the periodic table in the catalyst containing the medium pore diameter zeolite includes containing a group IB metal element in zeolite or the catalyst containing the medium pore diameter zeolite. Although there are no particular limitations on the method used, examples of methods that can be used include a method in which a zeolite or a catalyst containing a medium pore diameter zeolite, not containing a group IB metal element, is treated with a known ion exchange method, a liquid-phase ion exchange method and a method in which solid-state ion exchange treatment is carried out by treating an impregnated catalyst at a high temperature. In the case of containing a group IB metal in zeolite or zeolite-containing catalyst by the ion exchange method, it is necessary to use a salt of the group IB metal. Examples of salts of group IB metals include silver nitrate, silver acetate, silver sulfate, copper chloride, copper sulfate, copper nitrate and gold chloride. The salt of a group IB metal is preferably silver nitrate or copper nitrate, and more preferably silver nitrate. The content of group IB metal in the medium pore diameter zeolite is preferably 0.1 to 10% by weight. In addition, the content thereof can be determined by a known method such as X-ray fluorescence spectroscopy.

At least a portion of the ion exchange sites of the zeolite contained in the catalyst containing the medium pore diameter zeolite is preferably replaced with a group IB metal cation and/or proton. In addition, ion exchange sties other than those replaced with a group IB metal cation and/or proton may be replaced with alkaline metal cations, alkaline earth metal cations and other metal cations.

EXAMPLES

Hereinafter, the present embodiment is described more specifically with reference to Examples, but the present embodiment is not limited only to these Examples.

It is to be noted herein that the zeolite hydrothermal synthesis method, mechanical de-aggregating method, evaluation methods and measurement methods used in the present embodiment are as follows.

(Zeolite Hydrothermal Synthesis Method)

Zeolite used as a raw material of Example 1 was hydrothermally synthesized in the same manner as Example 2 of Japanese Patent Publication No. S61-21985 (Japanese Patent Application Laid-open No. S50-5335) with the exception of determining the amounts of a solution A containing $Al_2(SO_4)_3 \cdot xH_2O$ and a solution B containing sodium silicate so that the molar ratio of $SiO_2/Al_2O_3$ was 150 (the concentrations of each component in solution A and solution B were the same as Example 2 of the same publication).

Zeolite was hydrothermally synthesized in the same manner as Example 3 of Japanese Patent Publication No. H2-44771 (Japanese Patent Application Laid-open No. S59-54620) with the exception of preparing a homogeneous wet cake of compound D so that the molar ratio of $SiO_2/Al_2O_3$ was 27, and this was used as raw materials of Examples 2 and 5 and Comparative Examples 1 and 2.

Zeolite was hydrothermally synthesized in the same manner as Example 2 of Japanese Patent Publication No. S61-21985 with the exception of determining the amounts of solutions A and B so that the molar ratio of $SiO_2/Al_2O_3$ was 280, and this was used as raw materials of Examples 3 and 4.

Zeolites hydrothermally synthesized in the manner described above were dried at 120° C. after adequately rinsing with water, and each was determined to be MFI-type ZSM-5 as a result of measuring the structure type of the zeolites using a powder X-ray diffraction system (RINT, Rigaku Corp.). In addition, all of the zeolites were of the aggregating type zeolite, having an aggregation ratio of 80% or more.

(Zeolite $SiO_2/Al_2O_3$ Molar Ratio)

The zeolites were dissolved in an aqueous alkaline solution and the resulting solutions were subjected to quantitative analysis for silicon and aluminum by Inductively coupled plasma atomic emission spectrometry. The molar ratios of $SiO_2/Al_2O_3$ were determined from these values by calculation.

(Zeolite De-Aggregating Method)

Hydrothermally synthesized zeolite particles were subjected to mechanical de-aggregating treatment using a supersonic jet mill (Model LJ, by Nippon Pneumatic Mfg. Co., Ltd.). De-aggregating treatment was carried out under conditions consisted of a compressed air consumption rate of 0.4 $Nm^3$/min and de-aggregating treatment rate of 0.2 to 1.0 kg/hr until the mean particle diameter of the zeolites reached 2.9 μm or 8.9 μm, respectively.

(Composition of Catalyst Containing Medium Pore Diameter Zeolite)

In the case of the catalyst containing the medium pore diameter zeolite not containing aluminum other than zeolite, the composition of the catalyst containing the medium pore diameter zeolite can be calculated by X-ray fluorescent analysis. The composition were determined by measuring the number of moles of silicon, aluminum and phosphorous from the characteristic X-ray intensities of each of the elements of silicon, aluminum and phosphorous.

A indicating ratio of weight of silica to weight of zeolite $$=(60x-30Fy)/(51y+30Fy)$$

B indicating weight ratio of elementary phosphorous to total weight of zeolite and silica $$=31z/((51y+30Fy)+(60x-30Fy))$$

(In the formulas, x represents the number of moles of silicon in the catalyst containing the medium pore diameter zeolite, y represents the number of moles of aluminum in the catalyst containing the medium pore diameter zeolite, z represents the number of moles of phosphorous in the catalyst containing the medium pore diameter zeolite, and F represents the molar ratio of $SiO_2/Al_2O_3$ of the zeolite.)

(Weight-Based Particle Size Distribution)

The proportion of particles having a pore diameter of less than 10 μm and the proportion of particles having a particle diameter in excess of 197 μm in the catalyst particles were determined by measuring the weights of catalyst particles that passed through a sieve having a pore size of 10 μm and catalyst particles that were unable to pass through a sieve having a pore size of 197 μM using Micro Mesh High Precision Sieves manufactured by Buckbee Mears Co., St. Paul, Minn., USA, followed by determining the proportion of catalyst particles within the range of 10 to 197 μm from these values.

(Bulk Density)

Bulk density was measured using the Z-2504 bulk density measuring instrument manufactured by Tsutsui Scientific and Chemical Instruments Co., Ltd.

(Compressive Strength of Catalyst Particles)

Compressive strength was measured under the following conditions using the MCT-W500 Microcompression Tester manufactured by Shimadzu Corp.

Indenter: Top pressing indenter, diamond, 200 μm flat indenter

Lower pressing plate: SUS plate
Load speed: 19.4 mN/sec

Furthermore, particle diameter was taken to be the diameter of the particles determined by measuring the diameters in the vertical and horizontal directions and taking the average value thereof.

(Angle of Repose)

Angle of repose was measured using the Model PT-D Powder Tester (Hosokawa Micron Corp.). More specifically, a funnel having a nozzle having an inner diameter of 5 mm was installed using a retainer so that the top of the funnel was located 225 mm from a horizontal substrate and the bottom of the nozzle was located 135 mm from the horizontal substrate, and a powder capturing stand was placed at a location 75 mm from the bottom of the nozzle. While being careful not to generate vibrations, a catalyst containing a medium pore diameter zeolite was gently poured into the funnel and the angle formed between the inclined surface of the conical powder layer formed on the powder capturing stand and the horizontal surface was measured. The same experiment was repeated three times and the average value of the measured angles was taken to be the angle of repose.

(Catalyst Particle Attrition Loss)

Attrition loss serving as standard attrition loss of the catalyst particles was measured using a jet stream flow apparatus. The jet stream flow apparatus was composed of a powder rising unit, having an inner diameter of 35 mm and length of 700 mm provided with an orifice having three 0.4 mm holes in the gas inlet, a powder separation unit having an inner diameter of 110 mm and length of 600 mm, and a fine powder capturing unit. After loading 52.5 g of a catalyst containing a medium pore diameter zeolite containing 2.5 g of moisture at room temperature, air containing moisture in an amount corresponding to the vapor pressure was allowed to flow in from a gas inlet at a linear velocity of 10 cm/sec followed by measurement of the weight of fine powder of the catalyst containing the medium pore diameter zeolite recovered in the fine powder capturing unit from 0 to 5 hours and from 5 to 20 hours after the start of measurement, and determining the attrition loss using the formula:

$$\text{attrition loss (wt \%)} = D/(E-C) \times 100 \quad \text{Formula (5)}$$

(wherein, C represents the weight (g) of catalyst particles lost in 0 to 5 hours, D represents the weight (g) of catalyst particles lost in 5 to 20 hours, and E represents the weight (g) of the catalyst particles used in the test).

(Shape of Catalyst Particles)

The shape of the catalyst particles was observed with an electron microscope (SEM, S-800, Hitachi, Ltd.).

(Zeolite Mean Particle Diameter)

The mean particle diameter of the zeolites was measured using a laser diffraction/scattering particle size distribution analyzer (MT3000, Microtrac Corp.) in accordance with the manual provided by the manufacturer.

(Zeolite Aggregation)

Zeolite aggregation was calculated according to the formula below based on microscopic field images obtained using an electron microscope (SEM, S-800, Hitachi, Ltd.), and zeolite having an aggregation ratio of 50% or less was defined as non-aggregating zeolite.

Aggregation ratio=No. of zeolite particles partially bound to other primary particles/100 arbitrary zeolite particles×100

(Pore Volume of Catalyst Containing Medium Pore Diameter Zeolite)

Pore volume was measured over a mercury feed pressure range of 3.5 kPa to 231 MPa using a mercury intrusion porosimetry method particle size analyzer (PoreMaster 33PGT, Yuasa Ionics Inc.) and a sample size of about 0.1 g in accordance with the manual provided by the manufacturer.

(Ethylene/Propylene Measurement Method)

Ethylene and propylene were analyzed using a gas chromatograph in which TCD-FID were connected in series. The ethylene conversion was determined from formula (3), while the propylene yield was determined from formula (4).

Ethylene conversion=[(wt % of ethylene in gas supplied to inlet of fluidized bed reactor)−(wt % of ethylene in gas discharged from outlet of fluidized bed reactor)]/(wt % of ethylene in gas supplied to inlet of fluidized bed reactor)×100　　Formula (3)

Propylene yield=[(wt % of propylene in gas discharged from outlet of fluidized bed reactor)−(wt % of propylene in gas supplied to inlet of fluidized bed reactor)]/(wt % of ethylene in gas supplied to inlet of fluidized bed reactor)×100　　Formula (4)

(Silica Mean Particle Diameter)

The mean particle diameter of silica was measured using a laser diffraction/scattering particle size distribution analyzer (MT3000, Microtrac Corp.) in accordance with the manual provided by the manufacturer.

Example 1

Figure 1:
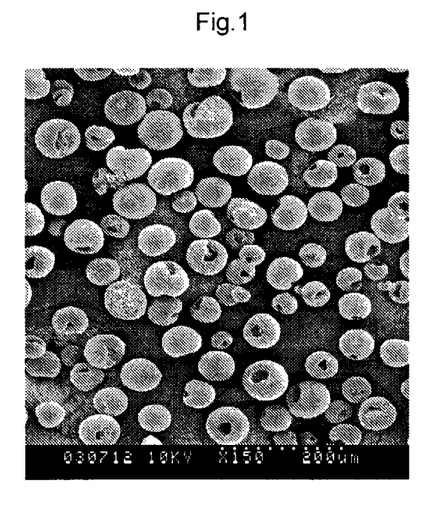
FIG. 1 shows an electron micrograph in which catalyst particles of Example 1 were observed with an electron microscope (magnification factor: 150×)

500 g of non-aggregating zeolite (MFI-type ZSM-5, $SiO_2/Al_2O_3$ molar ratio: 150, mean particle diameter: 8.9 μm, zeolite aggregation ratio: 10% or less) were added to 3333 g of ammonia-stabilized silica sol in which a mean particle diameter of silica primary particles was 5 nm (silica: 15% by weight) followed by stirring for 2 hours in air at room temperature. The resulting raw material mixture was spray-dried at a supply rate of 12 Kg/hr and rotating disc speed of 12000 rpm while introducing dry air so that the inlet gas temperature of a rotating disc-type spray dryer was maintained at about 180° C. and the outlet gas temperature was maintained at about 100° C. The resulting dry powder was calcined in a muffle furnace for 5 hours in air at 700° C. to obtain a catalyst containing a medium pore diameter zeolite having a composite ratio of zeolite to silica of 1/A (A=1). Furthermore, the charged composition and the composition as determined by analysis were the same. An SEM micrograph of the catalyst particles is shown in FIG. 1. In the resulting catalyst containing the medium pore diameter zeolite, the percentage of catalyst particles having a particle diameter within the range of 10 to 197 μm was 96.2% by weight, the bulk density was 0.79 g/cm³, the mean compressive strength of catalyst particles in which the particle diameter thereof was within the range of 30 to 70 μm was 26.8 MPa, the percentage of catalyst particles having a compressive strength of 10 MPa or more was 94%, the angle of repose was 27°, the pore volume of pores having a pore radius within the range of 2000 to 20000 nm is 0.001 cc/g, and the attrition loss was 0.9%.

Comparative Example 1

Figure 2:
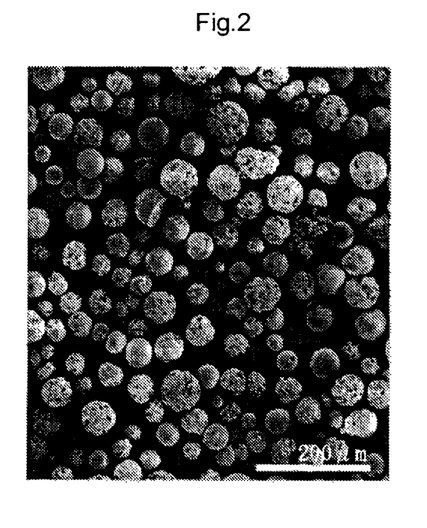
FIG. 2 shows an electron micrograph in which catalyst particles of Comparative Example 1 were observed with an electron microscope (magnification factor: 200×)

A catalyst containing a medium pore diameter zeolite and having a composite ratio of zeolite to silica of 1/A (A=1) were obtained in the same manner as Example 1 with the exception of using aggregating zeolite (MFI-type ZSM-5, $SiO_2/Al_2O_3$ molar ratio: 27, mean particle diameter: 15 μm, zeolite aggregation ratio: 80% or more) instead of the zeolite in Example 1, and calcining at 850° C. Furthermore, the charged composition and the composition as determined by analysis were the same. An SEM micrograph of the catalyst particles is shown in FIG. 2. In the resulting catalyst containing the medium pore diameter zeolite, the percentage of catalyst particles having a particle diameter within the range of 10 to 197 μm was 97.7% by weight, the bulk density was 0.53 g/cm$^3$, the mean compressive strength of catalyst particles in which the particle diameter thereof was within the range of 30 to 70 μm was 8.0 MPa, the percentage of catalyst particles having a compressive strength of 10 MPa or more was 40%, the angle of repose was 31°, and the pore volume of pores having a pore radius within the range of 2000 to 20000 nm is 0.236 cc/g. Although the attrition loss of these catalyst particles was attempted to be measured, since attrition loss of 31% occurred by 5 hours after the start of testing, measurement was discontinued at that point.

Example 2

Figure 3:
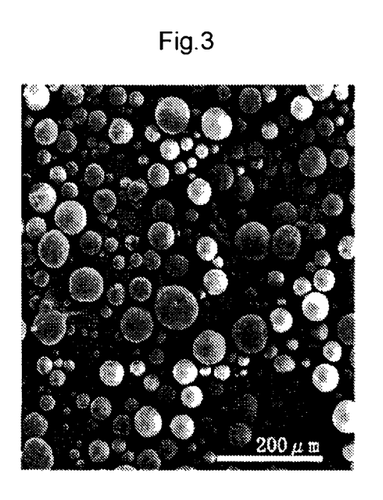
FIG. 3 shows an electron micrograph in which catalyst particles of Example 2 were observed with an electron microscope (magnification factor: 200×).

A catalyst containing a medium pore diameter zeolite having a composition in which a ratio of zeolite/silica/phosphorous is 1/A/B (A=1, B=0.024) was obtained in the same manner as Example 1 with the exception of using a non-aggregating zeolite (MFI-type ZSM-5, SiO$_2$/Al$_2$O$_3$ molar ratio: 27, mean particle diameter: 2.9 μm, zeolite aggregation ratio: 10% or less), adding 77 g of phosphoric acid and making the calcining temperature 850° C. Furthermore, the charged composition and the composition as determined by analysis were the same. An SEM micrograph of the catalyst particles is shown in FIG. 3. In the resulting catalyst containing the medium pore diameter zeolite, the percentage of catalyst particles having a particle diameter within the range of 10 to 197 μm was 96.8% by weight, the bulk density was 0.91 g/cm$^3$, the mean compressive strength of catalyst particles in which the particle diameter thereof was within the range of 30 to 70 μm was 24.6 MPa, the percentage of catalyst particles having a compressive strength of 10 MPa or more was 100%, the angle of repose was 26°, the pore volume of pores having a pore radius within the range of 2000 to 20000 nm is 0.015 cc/g, and the attrition loss was 0.3%.

Rinsing of this catalyst containing the medium pore diameter zeolite with water was carried out in the following manner. Water was added so that the concentration of catalyst containing the medium pore diameter zeolite was 10% by weight, and the resulting catalyst slurry containing the medium pore diameter zeolite was stirred for 1 hour in air at room temperature. The catalyst containing the medium pore diameter zeolite was then filtered and dried for 5 hours at 120° C. in air to obtain the catalyst containing the medium pore diameter zeolite in which a ratio of zeolite/silica/phosphorous was 1/A/B (A=1, B=0.019).

Example 3

A catalyst containing a medium pore diameter zeolite having a composition in which a ratio of zeolite/silica/phosphorous is 1/A/B (A=1, B=0.024) was obtained in the same manner as Example 1 with the exception of using a non-aggregating zeolite (MFI-type ZSM-5, SiO$_2$/Al$_2$O$_3$ molar ratio: 280, mean particle diameter: 2.9 μm, zeolite aggregation ratio: 10% or less), adding 77 g of phosphoric acid and making the calcining temperature 850° C. Furthermore, the charged composition and the composition as determined by analysis were the same. In the resulting catalyst containing the medium pore diameter zeolite, the percentage of catalyst particles having a particle diameter within the range of 10 to 197 μm was 95.5% by weight, the bulk density was 0.83 g/cm$^3$, the mean compressive strength of catalyst particles in which the particle diameter thereof was within the range of 30 to 70 μm was 24.9 MPa, the percentage of catalyst particles having a compressive strength of 10 MPa or more was 100%, the angle of repose was 28°, the pore volume of pores having a pore radius within the range of 2000 to 20000 nm is 0.002 cc/g, and the attrition loss was 0.4%.

Rinsing of this catalyst containing the medium pore diameter zeolite with water was carried out in the following manner. Water was added so that the concentration of catalyst containing the medium pore diameter zeolite was 10% by weight, and the resulting catalyst slurry containing the medium pore diameter zeolite was stirred for 1 hour in air at room temperature. The catalyst containing the medium pore diameter zeolite was then filtered and dried for 5 hours at 120° C. in air to obtain the catalyst containing the medium pore diameter zeolite in which a ratio of zeolite/silica/phosphorous was 1/A/B (A=1, B=0.018).

Example 4

A catalyst containing a medium pore diameter zeolite having a composition in which a ratio of zeolite/silica is 1/A (A=1) was obtained in the same manner as Example 1 with the exception of using a non-aggregating zeolite (MFI-type ZSM-5, SiO$_2$/Al$_2$O$_3$ molar ratio: 280, mean particle diameter: 2.9 μm, zeolite aggregation ratio: 10% or less) and calcining at the temperature of 800° C. for three hours. Furthermore, the charged composition and the composition as determined by analysis were the same. After washing 100 g of the resulting catalyst for 1 hour at room temperature using 1000 ml of 1 N aqueous nitric acid, the catalyst was contacted with 1000 ml of 1 N aqueous sodium nitrate solution for 1 hour at room temperature. After repeating this treatment with aqueous sodium nitrate solution additional two times, the catalyst was contacting with 1000 ml of 0.001 N aqueous silver nitrate solution for 1 hour at room temperature, then dried to obtain 100 g of catalyst particles containing 0.1% by weight of Ag. In the finally obtained catalyst containing the medium pore diameter zeolite, the percentage of catalyst particles having a particle diameter within the range of 10 to 197 μm was 96.0% by weight, the bulk density was 0.75 g/cm$^3$, the mean compressive strength of catalyst particles in which the particle diameter thereof was within the range of 30 to 70 μm was 18.5 MPa, the percentage of catalyst particles having a compressive strength of 10 MPa or more was 92%, the angle of repose was 29°, the pore volume of pores having a pore radius within the range of 2000 to 20000 nm is 0.020 cc/g, and the attrition loss was 2.3%.

Example 5

A catalyst containing a medium pore diameter zeolite having a composition in which a ratio of zeolite/silica/phosphorous is 1/NB (A=1, B=0.024) was obtained according to the same method as Example 2 with the exception of using 1667 g of a potassium-stabilized silica sol in which a mean particle diameter of silica primary particles was 20 nm and having a broad particle size distribution of 10 to 40 nm (silica: 30% by weight). Furthermore, the charged composition and the composition as determined by analysis were the same. In the resulting catalyst containing the medium pore diameter zeolite, the percentage of catalyst particles having a particle diameter within the range of 10 to 197 μm was 96.5% by weight, the bulk density was 0.89 g/cm$^3$, the mean compressive strength of catalyst particles in which the particle diameter thereof was within the range of 30 to 70 μm was 25.2 MPa, the percentage of catalyst particles having a compressive strength of 10 MPa or more was 100%, the angle of repose was 24°, the pore volume of pores having a pore radius within the range of 2000 to 20000 nm is 0.003 cc/g, and the attrition loss was 0.2%.

Comparative Example 2

A catalyst containing a medium pore diameter zeolite having a composition in which a ratio of zeolite/silica/phosphorous is 1/A/B (A=1, B=0.024) was obtained according to the same method as Example 5 with the exception of using 1667 g of an ammonium-stabilized silica sol in which a mean particle diameter of silica primary particles was 80 (silica: 30% by weight). Furthermore, the charged composition and the composition as determined by analysis were the same. In the resulting catalyst containing the medium pore diameter zeolite, the percentage of catalyst particles having a particle diameter within the range of 10 to 197 µm was 94.5% by weight, the bulk density was 0.79 g/cm$^3$, the mean compressive strength of catalyst particles in which the particle diameter thereof was within the range of 30 to 70 µm was 8.3 MPa, the percentage of catalyst particles having a compressive strength of 10 MPa or more was 42%, the angle of repose was 29°, and the pore volume of pores having a pore radius within the range of 2000 to 20000 nm is 0.180 cc/g. Although the attrition loss of these catalyst particles was attempted to be measured, since attrition loss of 28% occurred by 5 hours after the start of testing, measurement was discontinued at that point.

Example 6

21.6 g of the catalyst containing the medium pore diameter zeolite obtained in Example 1 were filled into a stainless steel fluidized bed reactor having an inner diameter of one inch, and a raw material gas was supplied to the reactor at flow rates of 9.9 g/hr for ethylene, 0.7 g/hr for hydrogen and 12.9 g/Hr for nitrogen followed by carrying out the reaction under conditions consisting of a reaction temperature of 550° C., reaction pressure of 0.14 MPaG, and WHSV of 0.49 (1/Hr). The reaction product was analyzed with a liquid chromatograph (TCD-FID connected in series) coupled directly to the reactor. 11 hours after the start of the reaction, the ethylene conversion was 78.1% and the propylene yield was 18.9%, 21 hours after the start of the reaction the ethylene conversion was 72.0% and the propylene yield was 20.2%, 33 hours after the start of the reaction the ethylene conversion was 66.3% and the propylene yield was 19.8%, and 48 hours after the start of the reaction the ethylene conversion was 58.7% and the propylene yield was 19.6%.

Example 7

24.0 g of the catalyst containing the medium pore diameter zeolite obtained in Example 2 were filled into a stainless steel fluidized bed reactor having an inner diameter of one inch, and a raw material gas was supplied to the reactor at flow rates of 16.6 g/hr for ethanol and 12.6 g/Hr for nitrogen followed by carrying out the reaction under conditions consisting of a reaction temperature of 550° C., reaction pressure of 0.14 MPaG, and WHSV of 0.69 (1/Hr). Since ethanol was not detected in the reaction gas, calculation of conversion was based on ethylene. 12 hours after the start of the reaction, the ethylene conversion was 75.5% and the propylene yield was 22.4%, 24 hours after the start of the reaction the ethylene conversion was 69.5% and the propylene yield was 22.8%, and 36 hours after the start of the reaction the ethylene conversion was 61.0% and the propylene yield was 22.2%.

Example 8

21.3 g of the catalyst containing the medium pore diameter zeolite obtained in Example 3 were filled into a stainless steel fluidized bed reactor having an inner diameter of one inch, and a raw material gas was supplied to the reactor at flow rates of 5.2 g/hr for ethylene, 1.3 g/hr for 1-butene, 0.5 g/hr for hydrogen, 3.3 g/hr for water and 3.5 g/Hr for nitrogen followed by carrying out the reaction under conditions consisting of a reaction temperature of 550° C., reaction pressure of 0.14 MPaG, and WHSV of 0.33 (1/Hr). In this reaction, the reaction raw materials were supplied at a ratio of ethylene to 1-butene of 80:20 (weight ratio). 3 hours after the start of the reaction, the ethylene conversion was 63.3% and the propylene yield was 21.2%, 9 hours after the start of the reaction the ethylene conversion was 60.2% and the propylene yield was 21.0%, and 18.5 hours after the start of the reaction the ethylene conversion was 56.3% and the propylene yield was 20.8%.

Example 9

24.9 g of the catalyst containing the medium pore diameter zeolite obtained in Example 2 were filled into a stainless steel fluidized bed reactor having an inner diameter of one inch, and a raw material gas was supplied to the reactor at flow rates of 9.9 g/hr for ethylene, 0.2 g/hr for acetylene, 0.7 g/hr for hydrogen and 12.6 g/Hr for nitrogen followed by carrying out the reaction under conditions consisting of a reaction temperature of 550° C., reaction pressure of 0.14 MPaG, and WHSV of 0.43 (1/Hr). In this reaction, acetylene was supplied to the reactor at a ratio of ethylene to acetylene of 98:2 (weight ratio). 24 hours after the start of the reaction, the ethylene conversion was 80.4% and the propylene yield was 20.5%, 33 hours after the start of the reaction the ethylene conversion was 75.3% and the propylene yield was 22.7%, and 44 hours after the start of the reaction the ethylene conversion was 62.5% and the propylene yield was 22.7%. At this point, the reaction was stopped and 7.5 g of the filled catalyst were extracted followed by calcining this catalyst for 2 hours at 580° C. in a muffle furnace in an air atmosphere. The carbonaceous compound removal rate of this catalyst was nearly 100%. This catalyst was again returned to the reactor and the reaction was resumed. 2 hours after the resumption of the reaction, the ethylene conversion was 77.3% and the propylene yield was 21.0%, 12 hours after the resumption of the reaction the ethylene conversion was 67.3% and the propylene yield was 22.1%, and 22 hours after the resumption of the reaction the ethylene conversion was 61.4% and the propylene yield was 21.7%.

Example 10

60 g of the catalyst containing the medium pore diameter zeolite obtained in Example 4 were filled into a stainless steel fluidized bed reactor having an inner diameter of one inch, and a raw material gas was supplied to the reactor at an ethylene flow rate of 90.0 g/hr followed by carrying out the reaction under conditions consisting of a reaction temperature of 550° C., reaction pressure of 0.01 MPaG, and WHSV of 1.5 (1/Hr). 1.5 hours after the start of the reaction, the ethylene conversion was 73.3% and the propylene yield was 21.0%, and 4 hours after the start of the reaction the ethylene conversion was 72.6% and the propylene yield was 22.5%.

Example 11

21.6 g of the catalyst containing the medium pore diameter zeolite obtained in Example 1 were filled into a stainless steel fluidized bed reactor having an inner diameter of one inch, and a raw material gas was supplied to the reactor at flow rates of 6.6 g/hr for ethylene, 5.4 g/hr for ethanol, 0.7 g/hr for hydrogen and 12.9 g/Hr for nitrogen followed by carrying out the reaction under conditions consisting of a reaction temperature of 550° C., reaction pressure of 0.14 MPaG, and WHSV of 0.49 (1/Hr). 12 hours after the start of the reaction, the ethylene conversion was 77.9% and the propylene yield was 18.8%, 23 hours after the start of the reaction the ethylene conversion was 71.7% and the propylene yield was 20.1%, and 37 hours after the start of the reaction the ethylene conversion was 65.9% and the propylene yield was 19.8%.

Example 12

Zeolite was hydrothermally synthesized in the same manner as Example 4 described in Japanese Patent Application Laid-open No. H10-52646 with the exception of setting a molar ratio of sodium silicate and $Al_2(SO_4)_3$ so that the molar ratio of $SiO_2/Al_2O_3$ was 39. The synthesized zeolite was a non-aggregating zeolite (MFI-type ZSM-5, $SiO_2/Al_2O_3$ molar ratio: 39, mean particle diameter: 3.3 μm, zeolite aggregation ratio: 10% or less).

A catalyst containing a medium pore diameter zeolite having a composition in which a ratio of zeolite/silica/phosphorous is 1/A/B (A=1, B=0.024) was obtained in the same manner as Example 3 with this non-aggregating zeolite. Furthermore, the charged composition and the composition as determined by analysis were the same.

In the resulting catalyst containing the medium pore diameter zeolite, the percentage of catalyst particles having a particle diameter within the range of 10 to 197 μm was 94.5% by weight, the bulk density was 0.84 g/cm³, the mean compressive strength of catalyst particles in which the particle diameter thereof was within the range of 30 to 70 μm was 23.9 MPa, the percentage of catalyst particles having a compressive strength of 10 MPa or more was 100%, the angle of repose was 28°, the pore volume of pores having a pore radius within the range of 2000 to 20000 nm is 0.002 cc/g, and the attrition loss was 0.8%.

Rinsing of this catalyst containing the medium pore diameter zeolite with water was carried out in the following manner. Water was added so that the concentration of catalyst containing the medium pore diameter zeolite was 10% by weight, and the resulting catalyst slurry containing the medium pore diameter zeolite was stirred for 1 hour in air at room temperature. The catalyst containing the medium pore diameter zeolite was then filtered and dried for 5 hours at 120° C. in air to obtain the catalyst containing the medium pore diameter zeolite in which a ratio of zeolite/silica/phosphorous was 1/A/B (A=1, B=0.019).

Example 13

21.6 g of the catalyst containing the medium pore diameter zeolite obtained in Example 12 were filled into a stainless steel fluidized bed reactor having an inner diameter of one inch, and a raw material gas was supplied to the reactor at flow rates of 9.9 g/hr for ethylene, 0.7 g/hr for hydrogen and 12.9 g/Hr for nitrogen followed by carrying out the reaction under conditions consisting of a reaction temperature of 550° C., reaction pressure of 0.14 MPaG, and WHSV of 0.49 (1/Hr). The reaction product was analyzed with a gas chromatograph (TCD-FID connected in series) coupled directly to the reactor. 11 hours after the start of the reaction, the ethylene conversion was 79.2% and the propylene yield was 19.1%, 21 hours after the start of the reaction the ethylene conversion was 74.0% and the propylene yield was 20.6%, 33 hours after the start of the reaction the ethylene conversion was 65.5% and the propylene yield was 19.0%, and 48 hours after the start of the reaction the ethylene conversion was 56.2% and the propylene yield was 18.0%.

In Examples 6 to 11 and 13, in which the catalyst containing the medium pore diameter zeolite that satisfied requirements (a) to (e) was used, propylene yields and ethylene conversion remained constant over time in all cases, thereby enabling stable production of propylene.

In addition, the catalysts containing the medium pore diameter zeolite of Examples 1 to 5 and 12, which were produced using the non-aggregating zeolite having the $SiO_2/Al_2O_3$ molar ratio of 15 to 1000 and the mean particle diameter of 0.05 to 10 μm, and the silica sol having the primary particle mean particle diameter of 3 to 50 μm, were all catalysts containing the medium pore diameter zeolite that satisfied requirements (a) to (e).

On the other hand, the catalyst containing the medium pore diameter zeolite of Comparative Example 1, which was produced using the aggregating zeolite having the mean particle diameter in excess of 10 μm, did not satisfy the requirements of (a) to (e), and demonstrated the extremely large value for attrition loss of 31%.

In addition, the catalyst containing the medium pore diameter zeolite of Comparative Example 2, which was produced using the silica sol having the primary particle mean particle diameter in excess of 50 μm, did not satisfy the requirements of (a) to (e), and demonstrated loss of 28% at 0 to 5 hours.

Since the catalysts containing the medium pore diameter zeolite of Comparative Examples 1 and 2 do not satisfy the requirements of (a) to (e), attrition loss exceeded 3%. Accordingly, since catalyst loss during production of propylene using a fluidized bed reactor is considered to be large, it is not possible to efficiently and stably produce propylene using the fluidized bed reactor with these catalysts.

The present application is based on Japanese Patent Application No. 2007-241434 filed on Sep. 18, 2007 and Japanese Patent Application No. 2008-064843 filed on Mar. 13, 2008, the contents of which are incorporated herein by reference.

INDUSTRIAL APPLICABILITY

The propylene production process of the present invention makes it possible to efficiently and stably produce propylene from ethylene and/or ethanol using a fluidized bed reactor. In addition, this process is useful as an industrial production process from the viewpoint of the diversity of the raw materials used for propylene production.

We claim:
1. A process for producing propylene, comprising contacting at least one of raw materials selected from the group consisting of ethylene and ethanol with a catalyst containing a medium pore diameter zeolite in a fluidized bed reactor wherein
the catalyst containing the medium pore diameter zeolite contains zeolite having a pore diameter of 0.5 to 0.65 nm and satisfies the following (a) through (f):
(a) a particle diameter of catalyst particles at 90% by weight or more is within a range of 10 to 197 μm;

(b) a bulk density of the catalyst particles is within a range of 0.7 to 1.1 g/cm$^3$;

(c) a mean compressive strength of the catalyst particles having a particle diameter within a range of 30 to 70 μm is 15 MPa or more, and a compressive strength of the catalyst particles at 90% by weight or more is 10 MPa or more;

(d) an angle of repose is 20 to 30°;

(e) a pore volume of pores having a pore radius within a range of 2000 to 20000 nm is 0.050 cc/g or less: and (f) contains a zeolite and a silica and has a composition represented by the following formula (1)

$$\text{zeolite/silica}=1/A \qquad (1)$$

(wherein A represents a ratio of a weight of the silica to a weight of the zeolite, and 0<A≤10), and is produced using a non-aggregating zeolite, in which a molar ratio of SiO$_2$/Al$_2$O$_3$ is 15 to 1000 and a mean particle diameter is 0.05 to 10 μm, and using a silica sol, in which a mean particle diameter of primary particles is 3 to 50 nm.

2. The process for producing propylene according to claim 1, further comprising steps of:

separating propylene from exit gas of the fluidized bed reactor; and recycling a portion or all of low boiling components containing ethylene in the exit gas and/or recycling a portion or all of high boiling components containing butene to the fluidized bed reactor.

3. The process for producing propylene according to claim 1, further comprising a step of: continuously or intermittently extracting a portion of the catalyst containing the medium pore diameter zeolite from the fluidized bed reactor, contacting with gas containing oxygen, burning carbonaceous compounds adhered to the catalyst containing a medium pore diameter zeolite, and supplying the medium pore diameter zeolite to the fluidized bed reactor following burning.

4. The process for producing propylene according to claim 1, wherein the catalyst containing the medium pore diameter zeolite contains a zeolite, a silica and a phosphorous, and has a composition represented by the following formula (2):

$$\text{zeolite/silica/phosphorous}=1/A/B \qquad (2)$$

(wherein A represents a ratio of a weight of the silica to a weight of the zeolite, B represents a ratio of a weight of elementary phosphorous to a total weight of the zeolite and the silica, 0<A ≤10 and 0<B ≤0.05), and is produced using a non-aggregating zeolite, in which a molar ratio SiO$_2$/Al$_2$O$_3$ is 15 to 1000 and a mean particle diameter is 0.05 to 10 μm, and using a silica sol, in which a mean particle diameter of primary particles is 3 to 50 nm.

5. The process for producing propylene according to claim 1, wherein the catalyst containing the medium pore diameter zeolite contains at least one of element selected from the group of elements belonging to group 1B of the periodic table.

6. A catalyst containing a medium pore diameter zeolite, which satisfies the following (a) through (e):

(a) a particle diameter of catalyst particles at 90% by weight or more is within a range of 10 to 197 μm;

(b) a bulk density of the catalyst particles is within a range of 0.7 to 1.1 g/cm$^3$;

(c) a mean compressive strength of the catalyst particles having a particle diameter within a range of 30 to 70 μm is 15 MPa or more, and a compressive strength of the catalyst particles at 90% by weight or more of is 10 MPa or more;

(d) an angle of repose is 20 to 30°; and (e) a pore volume of pores having a pore radius within a range of 2000 to 20000 nm is 0.050 cc/g or less.

7. The catalyst containing the medium pore diameter zeolite according to claim 6, wherein the catalyst contains a zeolite and a silica and has a composition represented by the following formula (1):

$$\text{zeolite/silica}=1/A \qquad (1)$$

(wherein A represents a ratio of a weight of the silica to a weight of the zeolite, and 0<A≤10), and the zeolite is a non-aggregating zeolite, in which a molar ratio of SiO$_2$/Al$_2$O$_3$ is 15 to 1000 and a mean particle diameter is 0.05 to 10 μm.

8. The catalyst containing the medium pore diameter zeolite according to claim 6, wherein the catalyst contains a zeolite, a silica and a phosphorous and has a composition represented by the following formula (2):

$$\text{zeolite/silica/phosphorous}=1/A/B \qquad (2)$$

(wherein A represents a ratio of a weight of the silica to a weight of the zeolite, B represents a ratio of a weight of elementary phosphorous to a total weight of the zeolite and the silica, 0<A ≤10 and 0<B≤0.05), and the zeolite is a non aggregating zeolite, in which a molar ratio of SiO$_2$/Al$_2$O$_3$ is 15 to 1000 and a mean particle diameter is 0.05 to 10 μm.

9. The catalyst containing the medium pore diameter zeolite according to claim 6, which contains at least one of element selected from the group of elements belonging to group IB of the periodic table.

10. A process for producing a catalyst containing a medium pore diameter zeolite, the process comprising the steps of:

(i) preparing a raw material mixture by mixing a non-aggregating zeolite, in which a molar ratio of SiO$_2$/Al$_2$O$_3$ is 15 to 1000 and a mean particle diameter s 0.05 to 10 μm and a silica sol, in which a mean particle diameter of primary particles is 3 to 50 nm; and (ii) obtaining a dry powder by spray-drying the raw material mixture.

11. A process for producing a catalyst containing a medium pore diameter zeolite, the process comprising the steps of:

(i) preparing a raw material mixture by mixing a non-aggregating zeolite, in which a molar ratio of SiO$_2$/Al$_2$O$_3$ is 15 to 1000 and a mean particle diameter is 0.05 to 10 μm, a silica sol, in which a mean particle diameter of primary particles is 3 to 50 nm, and a phosphate compound; and (ii) obtaining a dry powder by spray-drying the raw material mixture.

12. The catalyst containing the medium pore diameter zeolite according to claim 8, wherein the phosphorous is a water-soluble phosphorous compound.

13. The catalyst containing the medium pore diameter zeolite according to claim 8, wherein the phosphorous is a phosphoric acid.

14. The process for producing propylene according to claim 1, wherein the total content of ethylene and ethanol as ethylene based on the hydrocarbon compounds in the raw materials is 50% by weight or more.

15. The process for producing propylene according to claim 1, further comprising a step of:

synthesizing zeolite using a seed slurry and/or subjecting aggregating zeolite to treatment by de-aggregating, impacting, shearing, or alkaline solution to obtain the non-aggregating zeolite.

16. The process for producing propylene according to claim 4, further comprising a step of:
   synthesizing zeolite using a seed slurry and/or subjecting aggregating zeolite to treatment by de-aggregating, impacting, shearing, or alkaline solution to obtain the non-aggregating zeolite.

17. The process of producing propylene according to claim 1, wherein the medium pore diameter zeolite is ZSM-5.

\* \* \* \* \*